(12) United States Patent
Yuan

(10) Patent No.: US 7,374,897 B2
(45) Date of Patent: May 20, 2008

(54) ENZYME CYCLING BASED ASSAYS FOR ALPHA-METHYLACYL-COA RACEMASE

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 336 days.

(21) Appl. No.: 10/966,983

(22) Filed: Oct. 15, 2004

(65) Prior Publication Data

US 2006/0084132 A1 Apr. 20, 2006

(51) Int. Cl.
*C12Q 1/15* (2006.01)
(52) U.S. Cl. .................. 435/15; 435/25; 435/7.91
(58) Field of Classification Search .............. 435/15, 435/25, 7.91
See application file for complete search history.

(56) References Cited

U.S. PATENT DOCUMENTS

| 4,491,631 | A | 1/1985 | Imamura et al. | |
|---|---|---|---|---|
| 2002/0123081 | A1* | 9/2002 | Richardson et al. | 435/7.23 |
| 2003/0175736 | A1* | 9/2003 | Chinnaiyan et al. | 435/6 |
| 2004/0126761 | A1 | 7/2004 | Dobie et al. | |
| 2004/0152146 | A1* | 8/2004 | Wechter et al. | 435/15 |
| 2005/0136493 | A1 | 6/2005 | Rubin et al. | |
| 2006/0084133 | A1* | 4/2006 | Yuan | 435/25 |
| 2006/0211017 | A1 | 9/2006 | Chinnaiyan et al. | |

FOREIGN PATENT DOCUMENTS

WO WO-02/27324 4/2002

OTHER PUBLICATIONS

Jiang Z. et al. Discovery and Clinical Application of a Novel Prostate Cancer Marker. American Journal of Clinical Pathology Aug. 2004 122(2)275-289.*
Cuebas et al., Biochem. J. (2002) 363:801-807.
Cvetanovic et al., Biochemical J. (1985) 227:49-56.
Dommes et al., Eur. J. Biochem (1982) 125:335-341.
Ferdinandusse et al., J. Lipid Res. (2000) 41:1890-1896.
Kumar-Sinha et al., Am. J. Pathol. (2004) 164:787-793.
Luo et al., Cancer Res. (2002) 62:2220-2226.
Mizugaki et al., J. Biochem. (1982) 92:1649-1654.
Prasad et al., Arch. Biochem. Biophys. (1985) 237:535-544.
Rubin et al., JAMA (2002) 287:1662-1670.
Schmitz et al., Eur. J. Biochem. (1995) 231:815-822.
Schmitz et al., Eur. J. Biochem. (1994) 222:313-323.
Seubert et al., Biochim. Biophys. Acta (1968) 164:498-517.
Sreekumar et al., J. Nat'l. Cancer Inst. (2004) 96:834-843.
Veldhoven et al., Biochem. Biophys. Acta (1997) 1347:62-68.
Amery et al., J. Lipid Research (2000) 41:1752-1759.
International Search Report for PCT/US05/36983, mailed on Feb. 1, 2006, 3 pages.
Schmitz et al., Biochem. J. (1997) 326:883-889.
Restriction Requirement, from U.S. Appl. No. 11/004,477, mailed on Feb. 2, 2007.
Response to Restriction Requirement, from U.S. Appl. No. 11/004,477, filed Feb. 27, 2007.
Non-Final Rejection, from U.S. Appl. No. 11/004,477, mailed on Apr. 12, 2007.
Written Opinion for PCT/US05/36983, mailed on Feb. 1, 2006.
International Preliminary Report on Patentability for PCT/US05/36983, completed on Nov. 7, 2006.
Amendment in Response to Non-Final Office Action from U.S. Appl. No. 11/004.477, filed Jul. 11, 2007.
Notice of Allowance and Examiner's Amendment from U.S. Appl. No. 11/004,477, mailed on Aug. 10, 2007.

* cited by examiner

*Primary Examiner*—Ralph Gitomer
(74) *Attorney, Agent, or Firm*—Morrison & Foerster LLP

(57) ABSTRACT

The present invention provides a method for assaying alpha-methylacyl-CoA racemase activity. In the assay, a sample containing an alpha-methylacyl-CoA racemase or suspected of containing an alpha-methylacyl-CoA racemase is contacted with (2R)-pristanoyl-CoA. If alpha-methylacyl-CoA racemase is present in the sample, (2R)-pristanoyl-CoA is converted into (2S)-pristanoyl-CoA. The method then utilizes a cycling reaction system between (2S)-pristanoyl-CoA and trans-2,3-dehydropristanoyl-CoA to generate a detectable signal that corresponds to the alpha-methylacyl-CoA racemase activity. Kits for assaying alpha-methylacyl-CoA racemase based on the same principle are also provided.

19 Claims, No Drawings

ENZYME CYCLING BASED ASSAYS FOR ALPHA-METHYLACYL-CoA RACEMASE

FIELD OF THE INVENTION

This invention relates generally to the field of alpha-methylacyl-CoA racemase detection. In particular, the invention provides methods and kits for assaying alpha-methylacyl-CoA racemase in samples.

BACKGROUND OF THE INVENTION

Alpha-methylacyl-CoA racemase (AMACR) is a well-characterized enzyme which plays a key role in peroxisomal β-oxidation of dietary branched-chain fatty acids and C27-bile acid intermediates. Ferdinandusse et al., *J. Lipid Res.* 41:1890–1896 (2000). AMACR catalyzes the conversion of (R)-α-methyl-branched-chain fatty acyl-CoA esters to their (S)-stereoisomers. Cuebas et al., *Biochem. J.* 363:801–807 (2002); Schmitz et al., *Eur. J. Biochem.* 231:815–822 (1995). AMACR was isolated from human liver as a 47-kDa monomer and is mainly localized in peroxisomes with a small amount detected in the mitochondria. Schmitz et al., *Eur. J. Biochem.* 231:815–822 (1995); Schmitz et al., *Eur. J. Biochem.* 222:313–23 (1994). The isoelectric point for AMACR isolated from human liver is pH 6.1, and the enzyme is optimally active between pH 7 and pH 8.

Elevated expression of AMACR has been shown to be a biomarker for several types of cancer such as prostate, colorectal, ovarian, breast, bladder, lung, renal cell carcinoma, lymphoma, and melanoma. Rubin et al., *JAMA* 287: 1662–1670 (2002); Luo et al., *Cancer Res.* 62:2220–2226 (2002); Sreekumar et al., *J. Natl. Cancer Inst.* 96:834–843 (2004). Studies also show that alpha-methylacyl-CoA racemase enzymatic activity is elevated in prostate cancer tissue specimens. Kumar-Sinha et al., *Am. J. Pathol.* 164:787–93 (2004). PCT WO 02/27324 and U.S. Appl. Pub. 2002/0123081 describes methods for identifying patients having or at risk of developing prostate cancer and patients having or at risk of developing a cancer arising from metastasis of a prostate cancer to another tissue by measuring the expression or activity of AMACR.

Several methods have been reported for assaying enzymatic activity of AMACR. Schmitz et al. (*Eur. J. Biochem.* 222:313–23 (1994)) describe a radiometric assay for AMACR enzymatic activity, in which 2-methyl[2-(3)H] acyl-CoAs is used as substrate. Veldhoven et al. (Biochem. Biophys. Acta 1347:62–68 (1997)) describe an alternative enzymatic assay for AMACR, in which AMACR is combined with 2R-methyl-pentadecanoyl-CoA. The reaction product, a 2S-isomer, is desaturated by an excess of added oxidase (pristanoyl CoA oxidase) resulting in the production of hydrogen peroxide, which is monitored by means of peroxidase in the presence of a suitable hydrogen donor.

However, there is still a need for a reliable and sensitive method for assaying AMACR enzymatic activity in a sample (e.g., for diagnosing cancer).

BRIEF SUMMARY OF THE INVENTION

The invention provides methods for assaying an alpha-methylacyl-CoA racemase in a sample, said method comprises: a) contacting a sample suspected of containing an alpha-methylacyl-CoA racemase with (2R)-pristanoyl-CoA to generate (2S)-pristanoyl-CoA; b) converting said (2S)-pristanoyl-CoA from step a) if generated to trans-2,3-dehydropristanoyl-CoA in the presence of a (2S)-pristanoyl-CoA converting enzyme and a first electron acceptor in its oxidized form, whereby reduced form of the first electron acceptor is generated; said trans-2,3-dehydropristanoyl-CoA is converted back to (2S)-pristanoyl-CoA in the presence of a trans-2,3-dehydropristanoyl-CoA converting enzyme and a second electron acceptor in its reduced form to form a cycling reaction system, whereby oxidized form of the second electron acceptor is generated; wherein the first electron acceptor and the second electron acceptor are different; and c) assessing concentration change of the reduced or oxidized form of the first electron acceptor or the reduced or oxidized form of the second electron acceptor in said cycling reaction system, whereby the presence, absence and/or the amount of the alpha-methylacyl-CoA racemase in the sample is determined.

In some embodiments, the sample suspected of containing an alpha-methylacyl-CoA racemase is contacted with (2R)-pristanoyl-CoA, the (2S)-pristanoyl-CoA converting enzyme, and the first electron acceptor in its oxidized form. In other embodiments, the sample suspected of containing an alpha-methylacyl-CoA racemase is contacted with (2R)-pristanoyl-CoA, the (2S)-pristanoyl-CoA converting enzyme, the first electron acceptor in its oxidized form, the trans-2,3-dehydropristanoyl-CoA converting enzyme, and the second electron acceptor in its oxidized form.

In some embodiments, the (2S)-pristanoyl-CoA converting enzyme and the trans-2,3-dehydropristanoyl-CoA converting enzyme are different.

In some embodiments, the (2S)-pristanoyl-CoA converting enzyme is a pristanoyl-CoA dehydrogenase, and the first electron acceptor is selected from the group consisting of $NAD^+$, $NADP^+$, thio-$NAD^+$, thio-$NADP^+$, acetyl-$NAD^+$, and acetyl-$NADP^+$.

In some embodiments, the (2S)-pristanoyl-CoA converting enzyme is an acyl-CoA oxidase, and the first electron acceptor is $O_2$.

In some embodiments, the trans-2,3-dehydropristanoyl-CoA converting enzyme is a trans-2-enoyl-CoA reductase, and the second electron acceptor is selected from the group consisting of NADH, NADPH, thio-NADH, thio-NADPH, acetyl-NADH, and acetyl-NADPH.

In some embodiments, the (2S)-pristanoyl-CoA converting enzyme and the trans-2,3-dehydropristanoyl-CoA converting enzyme are the same. In some embodiments, both the (2S)-pristanoyl-CoA converting enzyme and the trans-2,3-dehydropristanoyl-CoA converting enzyme are pristanoyl-CoA dehydrogenase. In some embodiments, both the (2S)-pristanoyl-CoA converting enzyme and the trans-2,3-dehydropristanoyl-CoA converting enzyme are trans-2-enoyl-CoA reductase. The oxidized form of the first electron acceptor may be selected from the group consisting of $NAD^+$, $NADP^+$, thio-$NAD^+$, thio-$NADP^+$, acetyl-$NAD^+$, and acetyl-$NADP^+$, and the reduced form of the second electron acceptor may be selected from the group consisting of NADH, NADPH, thio-NADH, thio-NADPH, acetyl-NADH, and acetyl-NADPH.

The concentration change of the reduced or oxidized form of the first electron acceptor or the reduced or oxidized form of the second electron acceptor in said cycling reaction system may be assessed by photometric method.

The methods of the invention may further comprise a step of coupling the oxidized or reduced form of the first electron acceptor or the reduced or oxidized form of the second electron acceptor to a color-producing agent for assessing concentration change of the reduced or oxidized form of the first electron acceptor or the reduced or oxidized form of the second electron acceptor, wherein the concentration change of the oxidized or reduced form of the first electron acceptor or the reduced or oxidized form of the second electron acceptor is assessed by a colorimetric method.

The sample may be assayed by the methods of the invention includes a biological sample. In some embodiments, the biological sample is a biological fluid, such as blood, serum, plasma, and urine. In some embodiments, the biological sample is selected from the group consisting of prostate, colon, ovary, breast, bladder, lung, renal, lymphocytes.

The methods of the invention may be used for prognosis and/or diagnosis of cancer in an individual. In some embodiments, the cancer is selected from the group consisting of prostate cancer, colorectal cancer, ovarian cancer, breast cancer, bladder cancer, lung cancer, renal cancer, lymphoma, and melanoma. In some embodiments, the method of the invention is used for prognosis and/or diagnosis of prostate cancer in an individual by assaying alpha-methylacyl-CoA racemase activity in a blood sample (such as whole blood, plasma, and serum).

In some embodiments, the method further comprises a step of comparing the amount of alpha-methylacyl-CoA racemase in the sample from the individual to a predetermined value, whereby an increase of the amount of alpha-methylacyl-CoA racemase indicates the individual having or at risk of developing cancer. In some embodiments, the cancer is selected from the group consisting of prostate cancer, colorectal cancer, ovarian cancer, breast cancer, bladder cancer, lung cancer, renal cancer, lymphoma, and melanoma.

The invention also provide kits for assaying an alpha-methylacyl-CoA racemase in a sample, said kit comprises: (2R)-pristanoyl-CoA, a first electron acceptor in its oxidized form, a (2S)-pristanoyl-CoA converting enzyme which catalyzes conversion of (2S)-pristanoyl-CoA to trans-2,3-dehydropristanoyl-CoA in the presence of the first electron acceptor in its oxidized form, a second electron acceptor in its reduced form, and a trans-2,3-dehydropristanoyl-CoA converting enzyme which catalyzes conversion of trans-2,3-dehydropristanoyl-CoA to (2S)-pristanoyl-CoA in the presence of the second electron acceptor in its reduced form, wherein the first electron acceptor and the second electron acceptor are different.

In some embodiments, the (2S)-pristanoyl-CoA converting enzyme and trans-2,3-dehydropristanoyl-CoA converting enzyme are different. In some embodiments, the (2S)-pristanoyl-CoA converting enzyme is a pristanoyl-CoA dehydrogenase, and the first electron acceptor is selected from the group consisting of $NAD^+$, $NADP^+$, thio-$NAD^+$, thio-$NADP^+$, acetyl-$NAD^+$, and acetyl-$NADP^+$. In some embodiments, the (2S)-pristanoyl-CoA converting enzyme is an acyl-CoA oxidase, and the first electron acceptor is $O_2$. In some embodiments, the trans-2,3-dehydropristanoyl-CoA converting enzyme is a trans-2-enoyl-CoA reductase, and the second electron acceptor is selected from the group consisting of NADH, NADPH, thio-NADH, thio-NADPH, acetyl-NADH, and acetyl-NADPH.

In some embodiments, the (2S)-pristanoyl-CoA converting enzyme and trans-2,3-dehydropristanoyl-CoA converting enzyme are the same. In some embodiments, both the (2S)-pristanoyl-CoA converting enzyme and trans-2,3-dehydropristanoyl-CoA converting enzyme are pristanoyl-CoA dehydrogenase or trans-2-enoyl-CoA reductase, and the oxidized form of the first electron acceptor is selected from the group consisting of $NAD^+$, $NADP^+$, thio-$NAD^+$, thio-$NADP^+$, acetyl-$NAD^+$, and acetyl-$NADP^+$, and the reduced form of the second electron acceptor is selected from the group consisting of NADH, NADPH, thio-NADH, thio-NADPH, acetyl-NADH, and acetyl-NADPH.

The kit may further comprises an instruction indicating use for prognosis and/or diagnosis of cancer including, but not limited to, prostate cancer, colorectal cancer, ovarian cancer, breast cancer, bladder cancer, lung cancer, renal cancer, lymphoma, and melanoma.

DETAILED DESCRIPTION OF THE INVENTION

The present invention provides a method for assaying alpha-methylacyl-CoA racemase activity. In the assay, a sample containing alpha-methylacyl-CoA racemase or suspected of containing alpha-methylacyl-CoA racemase is contacted with (2R)-pristanoyl-CoA. If enzymatically active alpha-methylacyl-CoA racemase is present in the sample, (2R)-pristanoyl-CoA is converted into (2S)-pristanoyl-CoA. The method then utilizes a cycling reaction system between (2S)-pristanoyl-CoA and trans-2,3-dehydropristanoyl-CoA to generate a detectable signal that corresponds to the enzymatic activity of alpha-methylacyl-CoA racemase. The methods described herein can be used for diagnosing cancer. For example, the methods can be used for diagnosing prostate cancer using blood sample without biopsy.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "alpha-methylacyl-CoA racemase" or "AMACR" (EC 5.1.99.4) refers to an enzyme that catalyzes conversion between (2S)-2-methylacyl-CoA and (2R)-2-methylacyl-CoA. It is intended to encompass derivatives, variants, and analogs of alpha-methylacyl-CoA racemase that do not substantially alter its activity. Alpha-methylacyl-CoA racemase can be obtained from any sources, such as human, mouse, bovine, rat, fruit fly, etc.

As used herein, "(2S)-pristanoyl-CoA converting enzyme" refers to an enzyme which catalyzes formation of trans-2,3-dehydropristanoyl-CoA from (2S)-pristanoyl-CoA in the presence of an electron acceptor in its oxidized form. It is intended to encompass derivatives, variants, and analogs of (2S)-pristanoyl-CoA converting enzyme that do not substantially alter its activity.

As used herein, "trans-2,3-dehydropristanoyl-CoA converting enzyme" refers to an enzyme which catalyzes formation of (2S)-pristanoyl-CoA from trans-2,3-dehydropristanoyl-CoA in the presence of an electron acceptor in its reduced form. It is intended to encompass derivatives, variants, and analogs of trans-2,3-dehydropristanoyl-CoA converting enzyme that do not substantially alter its activity.

As used herein the term "assessing" is intended to include quantitative and qualitative determination in the sense of obtaining an absolute value for the amount or concentration of the analyte present in the reaction system, and also of obtaining an index, ratio, percentage, visual or other value indicative of the level of analyte in the reaction system. Assessment may be direct or indirect and the chemical species actually detected need not of course be the analyte itself but may for example be a derivative thereof or some further substance.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "blood sample" includes whole blood, serum, and plasma.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "fluid" refers to any composition that can flow. Fluids thus encompass compositions that are in the form of semi-solids, pastes, solutions, aqueous mixtures, gels, lotions, creams and other such compositions.

As used herein, "disease or disorder" refers to a pathological condition in an organism resulting from, e.g., infection or genetic defect, and characterized by identifiable symptoms.

As used herein, "contacting" means bringing two or more components together. "Contacting" can be achieved by mixing all the components in a fluid or semi-fluid mixture. "Contacting" can also be achieved when one or more components are brought into contact with one or more other components on a solid surface such as a solid tissue section or a substrate.

As used herein, a "cycling reaction system" refers to the process of converting (2S)-pristanoyl-CoA to trans-2,3-dehydropristanoyl-CoA and from trans-2,3-dehydropristanoyl-CoA back to (2S)-pristanoyl-CoA.

B. Methods for Assaying Alpha-methylacyl-CoA Racemase

The invention provides a method for assaying an alpha-methylacyl-CoA racemase in a sample, said method comprises: a) contacting a sample suspected of containing an alpha-methylacyl-CoA racemase with (2R)-pristanoyl-CoA to generate (2S)-pristanoyl-CoA; b) converting said (2S)-pristanoyl-CoA from step a) if generated to trans-2,3-dehydropristanoyl-CoA in the presence of a (2S)-pristanoyl-CoA converting enzyme and a first electron acceptor in its oxidized form, whereby reduced form of the first electron acceptor is generated; said trans-2,3-dehydropristanoyl-CoA is converted back to (2S)-pristanoyl-CoA in the presence of a trans-2,3-dehydropristanoyl-CoA converting enzyme and a second electron acceptor in its reduced form to form a cycling reaction system, whereby oxidized form of the second electron acceptor is generated; wherein the first electron acceptor and the second electron acceptor are different; and c) assessing concentration change of the reduced or oxidized form of the first electron acceptor or the reduced or oxidized form of the second electron acceptor in said cycling reaction system, whereby the presence, absence and/or the amount of the alpha-methylacyl-CoA racemase in the sample is determined. In some embodiments, the detectable signal generated in step c) is a concentration change of the reduced or oxidized form of the first electron acceptor or the reduced or oxidized form of the second electron acceptor in said cycling reaction system. In some embodiments, the sample is a blood sample (such as whole blood, serum, and plasma).

Step a): Converting (2R)-pristanoyl-CoA to (2S)-pristanoyl-CoA by an Alpha-methylacyl-CoA Racemase The methods for assaying an alpha-methylacyl-CoA racemase in the present invention are based on measuring an enzymatic activity catalyzed by an alpha-methylacyl-CoA racemase. Alpha-methylacyl-CoA racemases catalyze reactions which convert (2R)-pristanoyl-CoA to (2S)-pristanoyl-CoA. Accordingly, the presence or absence and the amount of an alpha-methylacyl-CoA racemase in a sample can be determined by determining the (2S)-pristanoyl-CoA generated in these reactions. Thus, an exemplary reaction scheme for step a) of the present invention is:

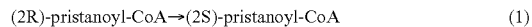

(2R)-pristanoyl-CoA→(2S)-pristanoyl-CoA         (1)

The (2R)-pristanoyl-CoA in step a) can be of any concentration that is suitable for an alpha-methylacyl-CoA racemase reaction and depends on the activity of the alpha-methylacyl-CoA racemase in the sample. For example, the concentration of (2R)-pristanoyl-CoA is about 0.01 mM to about 100 mM; about 0.05 mM to about 50 mM, about 0.5 mM to about 10 mM, or about 1 mM to about 5 mM. The enzymatic reaction is generally carried out in a condition (such as buffer and temperature) suitable for the completion of the enzymatic reactions. Any buffer known in the art suitable for alpha-methylacyl-CoA racemase enzymatic reaction can be used. For example, the buffer can be a phosphate buffer with a pH of about 6 to about 8; a Tris-HCl buffer with a pH of about 7 to about 9, or a Good's buffer with a pH of about 6 to about 9. For example, the reaction may be carried out at a temperature between about 30° C. to 37° C. for 5, 10, 15, 30, or 60 min. The reaction may be terminated before the next step.

Any sample containing or suspected of containing an alpha-methylacyl-CoA racemase can be assayed using the present invention. In some embodiments, the sample is blood (including whole blood, serum and plasma) or urine. In some embodiments, the sample is a tissue sample. In some embodiments, the tissue sample is subject to homogenization to obtain a crude tissue homogenate before the assay is conducted.

In some embodiments, the sample is pre-processed before the assay is carried out. Exemplary processing steps include centrifugation, extraction/washing, cell lysis, freeze/thaw, and sonication. The sample may also be diluted before the assay.

Step b): (2S)-pristanoyl-CoA/trans-2,3-dehydropristanoyl-CoA Cycling Reaction System Step b) of the present invention converts (2S)-pristanoyl-CoA to trans-2,3-dehydropristanoyl-CoA in the presence of a first electron acceptor (in its oxidized form) through the action of a (2S)-pristanoyl-CoA converting enzyme, and then from trans-2,3-dehydropristanoyl-CoA back to (2S)-pristanoyl-CoA in the presence of a second electron acceptor (in its reduced form) through the action of a trans-2,3-dehydropristanoyl-CoA converting enzyme. The first electron acceptor and the second electron acceptor are different electron acceptors. Step b) thus forms a cycling reaction system generating an increase of the first electron acceptor in its reduced form and a reduction of the first electron acceptor in its oxidized form, and an increase of the second electron acceptor in its oxidized form and a reduction of the second electron acceptor in its reduced form. The increase of an electron acceptor in a specific form or the reduction of an electron acceptor in a specific form can be measured. In some embodiments, an electron acceptor in a specific form is accumulated and the accumulation is assessed.

In some embodiments, the (2S)-pristanoyl-CoA converting enzyme and the trans-2,3-dehydropristanoyl-CoA converting enzyme are different. In some embodiments, the (2S)-pristanoyl-CoA converting enzyme does not cross-react with the second electron acceptor or binds to the second electron acceptor with a lower affinity than to the first electron acceptor, and/or the trans-2,3-dehydropristanoyl-CoA converting enzyme does not cross-react with the first electron acceptor or binds to the first electron acceptor with a lower affinity than to the first electron acceptor.

Any (2S)-pristanoyl-CoA converting enzyme that catalyzes formation of trans-2,3-dehydropristanoyl-CoA from (2S)-pristanoyl-CoA in the presence of an electron acceptor in its oxidized form can be used.

In some embodiments, the (2S)-pristanoyl-CoA converting enzyme is a pristanoyl-CoA dehydrogenase (EC 1.3.1.8). For example, any pristanoyl-CoA dehydrogenase (EC 1.3.1.8) having amino acid sequences with the following GenBank Accession No. B70719 (*Mycobacterium tuberculosis*), or described by Cvetanovic et al. (*Biochemical J.* 227:49–56 (1985)), Dommes et al. (*Eur. J. Biochem.* 125:335–341 (1982)), and Seubert et al. (*Biochim. Biophys. Acta* 164:498–517 (1968)) can be used.

In other embodiments, the (2S)-pristanoyl-CoA converting enzyme is an acyl-CoA oxidase (EC 1.3.3.6). For example, acyl-CoA oxidase (EC 1.3.3.6) having the amino acid sequence with the following GenBank Accession Nos. T52121 (*Arabidopsis thaliana*), T52120 (*Arabidopsis thaliana*), 138095 (*Homo sapiens*), S64224 (*Saccaromyces cerevisiae*), A54942 (*Homo sapiens*), OXRTA2 (*Rattus norveqicus*), OXRTA1 (*Rattus norveqicus*), OXCKX5 (*candida tropicalis*) can be used.

In still other embodiments, the (2S)-pristanoyl-CoA converting enzyme is a trans-2-enoyl-CoA reductase (EC 1.3.1.38). For example, any trans-2-enoyl-reductase (EC 1.3.1.38) having the amino acid sequence with the following GenBank Accession No S72400 (*Streptomyces collinus*), or described by Mizugaki et al. (*J. Biochem.* 92:1649–1654 (1982)) and Prasad et al. (*Arch. Biochem. Biophys.* 237:535–544 (1985)) can be used.

Any trans-2,3-dehydropristanoyl-CoA converting enzyme that catalyzes formation of (2S)-pristanoyl-CoA from trans-2,3-dehydropristanoyl-CoA in the presence of an electron acceptor in its reduced form can be used.

In some embodiments, the trans-2,3-dehydropristanoyl-CoA converting enzyme is a trans-2-enoyl-CoA reductase (EC 1.3.1.38). Any trans-2-enoyl-CoA reductase known in the art and described herein can be used.

In other embodiments, the trans-2,3-dehydropristanoyl-CoA converting enzyme is a pristanoyl-CoA dehydrogenase (EC 1.3.1.8). Any pristanoyl-CoA dehydrogenase known in the art and described herein can be used.

In some embodiments, the (2S)-pristanoyl-CoA converting enzyme and the trans-2,3-dehydropristanoyl-CoA converting enzyme are the same. In one embodiment, both the (2S)-pristanoyl-CoA converting enzyme and the trans-2,3-dehydropristanoyl-CoA converting enzyme are pristanoyl-CoA dehydrogenase. In other embodiment, both the (2S)-pristanoyl-CoA converting enzyme and the trans-2,3-dehydropristanoyl-CoA converting enzyme are trans-2-enoyl-CoA reductase. Any pristanoyl-CoA dehydrogenase and trans-2,3-dehydropristanoyl-CoA converting enzyme known in the art and described herein may be used.

The first and second electron acceptors can be any electron acceptors that are compatible with the enzymes chosen for the reactions, provided that the first electron acceptor and the second electron acceptor are different.

In some embodiments, the (2S)-pristanoyl-CoA converting enzyme is pristanoyl-CoA dehydrogenase and the first electron acceptor is selected from the group consisting of $NAD^+$, $NADP^+$, thio-$NAD^+$, thio-$NADP^+$, acetyl-$NAD^+$, and acetyl-$NADP^+$. In some embodiments, the (2S)-pristanoyl-CoA converting enzyme is acyl-CoA oxidase and the first electron acceptor is $O_2$. In some embodiments, the (2S)-pristanoyl-CoA converting enzyme is trans-2-enoyl-CoA reductase, and the first electron acceptor is selected from the group consisting of $NAD^+$, $NADP^+$, thio-$NAD^+$, thio-$NADP^+$, acetyl-$NAD^+$, and acetyl-$NADP^+$.

In some embodiments, the trans-2,3-dehydropristanoyl-CoA converting enzyme is trans-2-enoyl-CoA reductase, and the second electron acceptor is selected from the group consisting of NADH, NADPH, thio-NADH, thio-NADPH, acetyl-NADH, and acetyl-NADPH. In some embodiments, the trans-2,3-dehydropristanoyl-CoA converting enzyme is pristanoyl-CoA dehydrogenase and the second electron acceptor is selected from the group consisting of NADH, NADPH, thio-NADH, thio-NADPH, acetyl-NADH, and acetyl-NADPH.

In some embodiments, the (2S)-pristanoyl-CoA converting enzyme and the trans-2,3-dehydropristanoyl-CoA converting enzyme may collectively catalyze a cycling reaction between (2S)-pristanoyl-CoA and trans-2,3-dehydropristanoyl-CoA that amplifies signals generated in the assay. The (2S)-pristanoyl-CoA converting enzyme and the trans-2,3-dehydropristanoyl-CoA converting enzyme may utilize different electron acceptors and do not cross-react with electron acceptors used by the other enzyme or react with low affinity. Alternatively, the two enzymes may recognize the same electron acceptors. Sufficient amount of oxidized form of the first electron acceptor and reduced form of the second electron acceptor can be added to the cycling reaction to drive both reactions and allow the cycle to go on until sufficient signal is generated.

In the following two exemplary reaction schemes for step b), the (2S)-pristanoyl-CoA converting enzyme and the trans-2,3-dehydropristanoyl-CoA converting enzyme are different. For example, the (2S)-pristanoyl-CoA converting enzyme is pristanoyl-CoA dehydrogenase (EC 1.3.1.8) and the trans-2,3-dehydropristanoyl-CoA converting enzyme is trans-2-enoyl-CoA reductase (EC 1.3.1.38). Thus, an exemplary reaction scheme for step b) is:

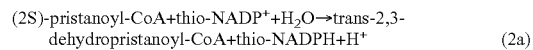

(2S)-pristanoyl-CoA+thio-$NADP^+$+$H_2O$→trans-2,3-dehydropristanoyl-CoA+thio-NADPH+$H^+$ (2a)

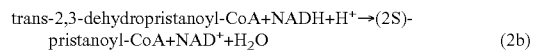

trans-2,3-dehydropristanoyl-CoA+NADH+$H^+$→(2S)-pristanoyl-CoA+$NAD^+$+$H_2O$ (2b)

Reaction (2a) represents a reaction catalyzed by a pristanoyl-CoA dehydrogenase, and reaction (2b) represents a reaction catalyzed by a trans-2-enoyl-CoA reductase. Sufficient thio-NADP+ and NADH can be added to the reaction to generate a cycling reaction, which leads to accumulation of thio-NADPH.

In another example, acyl-CoA oxidase (EC 1.3.3.6) is used as the (2S)-pristanoyl-CoA converting enzyme, and trans-2-enoyl-CoA reductase (EC 1.3.1.38) is used as the trans-2,3-dehydropristanoyl-CoA converting enzyme in the cycling reaction. An exemplary reaction scheme is:

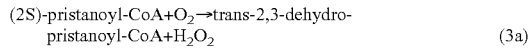

(2S)-pristanoyl-CoA+O₂→trans-2,3-dehydro-
pristanoyl-CoA+H₂O₂ (3a)

trans-2,3-dehydropristanoyl-CoA+NADPH+H+→
(2S)-pristanoyl-CoA+NADP++H₂O (3b)

Reaction (3a) represents a reaction catalyzed by an acyl-CoA oxidase, and reaction (3b) represents a reaction catalyzed by a trans-2-enoyl-CoA reductase. Sufficient amount of O₂ and NADPH can be added to the reaction to generate a cycling reaction, which leads to accumulation of NADP+ and H₂O₂.

The following is an exemplary reaction scheme, in which the (2S)-pristanoyl-CoA converting enzyme and the trans-2,3-dehydropristanoyl-CoA converting enzyme are the same. One such exemplary reaction scheme is:

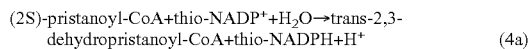

(2S)-pristanoyl-CoA+thio-NADP++H₂O→trans-2,3-
dehydropristanoyl-CoA+thio-NADPH+H+ (4a)

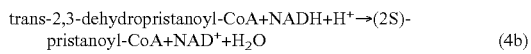

trans-2,3-dehydropristanoyl-CoA+NADH+H+→(2S)-
pristanoyl-CoA+NAD++H₂O (4b)

Both reaction (4a) and (4b) are catalyzed by the same enzyme, which is a pristanoyl-CoA dehydrogenase (EC 1.3.1.8) or a trans-2-enoyl-CoA reductase (EC 1.3.1.38). Sufficient thio-NADP+ and NADH can be added to the reaction mix to drive both reactions in a cycling reaction that leads to accumulation of thio-NADPH.

Any other combinations of (2S)-pristanoyl-CoA converting enzymes and trans-2,3-dehydropristanoyl-CoA converting enzymes may be used to achieve the same cycling effect.

The enzymatic reactions in steps a) and b) are generally carried out in a condition (such as buffer and temperature) suitable for the completion of the enzymatic reactions. The buffer used for step b) and step a) described herein can be the same or can be different. Any buffer known in the art suitable for the specific enzymatic reactions in step b) can be used. For example, the buffer can be a phosphate buffer with a pH of about 6 to about 8; a Tris-HCl buffer with a pH of about 7 to about 9, or a Good's buffer with a pH of about 6 to about 9.

The temperature for step b) can be the same or different from step a). The temperature in step b) is preferably between about 25° C. to about 37° C.

In some embodiments, one or more steps described herein are carried out in a separate reaction mixture. For example, the end products of one or more steps in the reaction can be partially or completely separated from the reaction mixture before reagents for the next step are added.

In some embodiments, steps a) and b) described herein are carried out in a single reaction mixture. In some embodiments, the enzymes, substrates, or electronic acceptors for the next step are added sequentially to the same reaction mix at the end of a previous step. In some embodiments, the reaction in a previous step is terminated before reagents for the next step are added. In some embodiment, some or all reagents for more than one steps are added simultaneously to the reaction mixture. In some embodiments, reagents for steps a) and b) are mixed with the sample at the same time.

In these embodiments, the sample suspected of containing an alpha-methylacyl-CoA racemase is contacted with (2R)-pristanoyl-CoA, a (2S)-pristanoyl-CoA converting enzyme, and the first electron acceptor in its oxidized form, a trans-2,3-dehydropristanoyl-CoA converting enzyme, and a second electron acceptor in its reduced form. In some embodiments, reagents for steps a) and some of the reagents for step b) are mixed with the sample at the same time. In these embodiments, the sample suspected of containing an alpha-methylacyl-CoA racemase is contacted with (2R)-pristanoyl-CoA, a (2S)-pristanoyl-CoA converting enzyme, a first electron acceptor in its oxidized form.

Step c): Assessing Signals Generated in Step b)

The quantification of alpha-methylacyl-CoA racemase in the sample can be achieved by monitoring the subtractive or additive difference in the signal generated in step b). The assessment can be carried out continuously or at different time points.

In some embodiments, the concentration change of the reduced or oxidized form of the first electron acceptor is assessed. In some embodiments, the activity of alpha-methylacyl-CoA racemase is determined by assessing an increase in concentration of the reduced form of the first electron acceptor. In some embodiments, the activity of alpha-methylacyl-CoA racemase is determined by assessing a decrease in concentration of the oxidized form of the first electron acceptor.

In some embodiments, the concentration change of the reduced or oxidized form of the second electron acceptor is assessed. In some embodiments, the activity of alpha-methylacyl-CoA racemase is determined by assessing a decrease in concentration of the reduced form of the second electron acceptor. In some embodiments, the activity of alpha-methylacyl-CoA racemase is determined by assessing an increase in concentration of the oxidized form of the second electron acceptor.

The concentration changes of electron acceptors described herein can be assessed using methods known in the art. For example, the concentration changes of NADH or NADPH can be determined spectrophotometrically by measuring the absorption at 340 nm. The concentration changes of thio-NADPH can be determined spectrophotometrically by measuring absorption at 405 nm.

In some embodiments, the concentration changes NADH or NADPH can be measured by colorimetric method using an electron transport chromogens, including, but not limited to, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 3,3'-(4,4'-biphenylene)-bis(2,5-diphenyl-2H-tetrazolium chloride), 3,3'-(3,3'-dimethoxy-4,4'-biphenylene)-bis[2-(p-nitrophenyl)-5-phenyl-2H-tetrazolium chloride](=nitro-tetrazolium: NTB), 3,3'-(3,3'-dimethoxy-4,4'biphenylene)-bis[2,5-bis(p-nitrophenyl)-2H-tetrazolium chloride], 3,3'-(3,3'-dimethoxy-4,4'-biphenylene)-bis(2,5-diphenyl-2H-tetrazolium chloride), and 2,6-dichlorophenol-indophenol. A preferred example is a combination of water-soluble tetrazolium salt and diaphorase or phenazinemethosulfate. These electron transport chromogens are electron acceptors for NADP or NADPH to form a colored formazane pigment, and the formed pigment is calorimetrically measured at the maximum absorption thereof.

A further assay method for NADH or NADPH is fluorometry wherein NAD or NADPH is treated with diaphorase in the presence of a fluorescent reagent such as resazulin.

Measurement of concentration of reduced and/or oxidized forms of electron acceptors described herein are known in the art. For example, the amount of consumed $O_2$ or $H_2O_2$ formed can be assayed by the use of electronic sensors. Numerous red-ox indicators can be used for this purpose, and a wide range of methods are described in the literature for assaying $H_2O_2$ and $O_2$ in solution. Generated $H_2O_2$ can also be measured as a detectable product by reacting with an indicator and $H_2O_2$. Examples of indicators are reagents which can be measured by spectrophotometric means, color indicators, fluorescent reagents or luminescent reagents. For example, $H_2O_2$ can be assessed using the non-enzymatic chemiluminescent reactions of peroxioxalate and the acridinium esters.

Assays may be performed in duplicates with both positive and background controls. A standard curve can be obtained by using known amounts of alpha-methylacyl-CoA racemase with known activity. The levels of alpha-methylacyl-CoA racemase in each sample can then be determined by comparing each signal measured to the standard curve.

C. Uses of the Methods

The present invention provides an assay with increased sensitivity for detecting alpha-methylacyl-CoA racemase present in a sample, such a blood sample. The methods of the invention thus provides a practical means for detecting conditions associated with altered levels of alpha-methylacyl-CoA racemase and monitoring alpha-methylacyl-CoA racemase levels in an individual. The method can be used for prognosis or diagnosis of any disease associated with an inappropriate amount or activity of alpha-methylacyl-CoA racemase, or the effect or activity of such, in a subject. Examples of such diseases include, but are not limited to, cancer such as prostate cancer, colorectal cancer, ovarian cancer, breast cancer, bladder cancer, lung cancer, renal cancer, lymphoma, and melanoma.

The enzymatic assay of the present invention also provides a research tool for the exploration of the role of alpha-methylacyl-CoA racemase in biological processes and various pathological conditions.

D. Kits for Assaying Alpha-methylacyl-CoA Racemase

The present invention also provides kits for assaying alpha-methylacyl-CoA racemase activities, such as a diagnostic kit. Such kits comprise one or more substrates, enzymatic agents and electron acceptors described herein for carrying out the methods of the present invention. In some embodiments, the kit comprises (2R)-pristanoyl-CoA, a (2S)-pristanoyl-CoA converting enzyme, a first electron acceptor in its oxidized form, a trans-2,3-dehydropristanoyl-CoA converting enzyme, and a second electron acceptor in its reduced form, wherein the first electron acceptor and the second electron acceptor are different. Any of the substrates, enzymes, and electron acceptors described herein may be included in the kit. The kits may also comprise positive and/or negative control standards, as well as necessary reagents for assessing the signals generated by step b), for example, reagents for conducting a colormetic assay may be included. The kits may also comprise an apparatus or container for conducting the methods of the invention and/or transferring samples to a diagnostic laboratory for processing, as well as suitable instructions for carrying out the methods of the invention.

The kits of the invention may be in any suitable packaging. For example, the packages discussed herein in relation to diagnostic systems are those customarily utilized in diagnostic systems. Such packages include containers appropriate for use in autoanalyzers.

E. EXAMPLES

The following examples are included for illustrative purposes only and are not intend to limit the scope of the invention.

Example 1

Alpha-methylacyl-CoA Racemase (AMACR) Assay Using Pristanoyl-CoA Dehydrogenase and Trans-2-enoyl-CoA Reductase In this study, the (2S)-pristanoyl-CoA converting enzyme is pristanoyl-CoA dehydrogenase; and the trans-2,3-dehydropristanoyl-CoA converting enzyme is trans-2-enoyl-CoA reductase. The reagents used in this study are set forth in the following Table 1 and Table 2.

TABLE 1

Compositions of Reagent 1

| Chemical Reagents | Concentration |
|---|---|
| Goods buffer, pH 6.0 | 50 mM |
| Pristanoyl-CoA dehydrogenase | 10 u/ml |
| Thio-$NAD^+$ | 1 mM |

TABLE 2

Compositions of Reagents 2

| Chemical Reagents | Concentration |
|---|---|
| Tris-HCl buffer, pH 8.5 | 100 mM |
| NADH | 2 mM |
| Trans-2-enoyl-CoA reductase | 10 u/ml |
| (2R)-pristanoyl-CoA | 30 mM |

In this study, 260 ul of Reagent 1 is added 20 ul of sample (serum or plasma). After 5 min incubation at 25° C. or 37° C., 60 ul of Reagent 2 is added to the reaction mixture. The absorbance change at 405 nm is monitored between 8 min and 10 min. The rate of increase at 405 nm is used for calculation of AMACR activity in sample against a rate generated from an AMACR calibrator.

Example 2

Alpha-methylacyl-CoA Racemase (AMACR) Assay Using Acyl-CoA Oxidase and Trans-2-enoyl-CoA Reductase In this study, the (2S)-pristanoyl-CoA converting enzyme is acyl-CoA oxidase; and the trans-2,3-dehydropristanoyl-CoA converting enzyme is trans-2-enoyl-CoA reductase. The reagents used in this study are set forth in the following Table 3 and Table 4.

TABLE 3

Compositions of Reagent 1

| Chemical Reagents | Concentration |
|---|---|
| Goods buffer, pH 7.0 | 50 mM |
| Acyl-CoA oxidase | 10 u/ml |
| N-ethyl-(2-hydroxy-3-sulfopropyl)-methylaniline (EHSPT) | 0.5 mM |

TABLE 3-continued

Compositions of Reagent 1

| Chemical Reagents | Concentration |
| --- | --- |
| 4'-aminoantipyrine | 1 mM |
| Peroxidase | 0.5 u/ml |

TABLE 4

Compositions of Reagents 2

| Chemical Reagents | Concentration |
| --- | --- |
| Tris-HCl buffer, pH 8.5 | 100 mM |
| NADPH | 2 mM |
| Trans-2-enoyl-CoA reductase | 15 u/ml |
| (2R)-pristanoyl-CoA | 30 mM |

In this study, 260 ul of Reagent 1 is added into 25 ul of sample (serum or plasma). After 5 min of incubation at 25° C. or 37° C., 60 ul of Reagent 2 is added to the reaction mixture. The absorbance change at 550 nm is monitored between 8 min to 10 min. The AMACR activity in the sample is calculated using an AMACR calibrator.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The claimed invention is:

1. A method for assaying an alpha-methylacyl-CoA racemase in a sample, said method comprises:
    a) contacting a sample suspected of containing an alpha-methylacyl-CoA racemase with (2R)-pristanoyl-CoA to generate (2S)-pristanoyl-CoA;
    b) converting said (2S)-pristanoyl-CoA from step a) if generated to trans-2,3-dehydropristanoyl-CoA in the presence of a (2S)-pristanoyl-CoA converting enzyme and a first electron acceptor in its oxidized form, whereby reduced form of the first electron acceptor is generated; said trans-2,3-dehydropristanoyl-CoA is converted back to (2S)-pristanoyl-CoA in the presence of a trans-2,3-dehydropristanoyl-CoA converting enzyme and a second electron acceptor in its reduced form to form a cycling reaction system, whereby oxidized form of the second electron acceptor is generated; wherein the first electron acceptor and the second electron acceptor are different; and
    c) assessing concentration change of the reduced or oxidized form of the first electron acceptor or the reduced or oxidized form of the second electron acceptor in said cycling reaction system, whereby the presence, absence and/or the amount of the alpha-methylacyl-CoA racemase in the sample is determined.

2. The method of claim 1, wherein the (2S)-pristanoyl-CoA converting enzyme and the trans-2,3-dehydropristanoyl-CoA converting enzyme are different.

3. The method of claim 2, wherein the (2S)-pristanoyl-CoA converting enzyme is a pristanoyl-CoA dehydrogenase, and the first electron acceptor is selected from the group consisting of $NAD^+$, $NADP^+$, thio-$NAD^+$, thio-$NADP^+$, acetyl-$NAD^+$, and acetyl-$NADP^+$.

4. The method of claim 2, wherein the (2S)-pristanoyl-CoA converting enzyme is an acyl-CoA oxidase, and the first electron acceptor is $O_2$.

5. The method of claim 2, wherein the trans-2,3-dehydropristanoyl-CoA converting enzyme is a trans-2-enoyl-CoA reductase, and the second electron acceptor is selected from the group consisting of NADH, NADPH, thio-NADH, thio-NADPH, acetyl-NADH, and acetyl-NADPH.

6. The method of claim 3, wherein the trans-2,3-dehydropristanoyl-CoA converting enzyme is a trans-2-enoyl-CoA reductase, and the second electron acceptor is selected from the group consisting of NADH, NADPH, thio-NADH, thio-NADPH, acetyl-NADH, and acetyl-NADPH.

7. The method of claim 4, wherein the trans-2,3-dehydropristanoyl-CoA converting enzyme is a trans-2-enoyl-CoA reductase, and the second electron acceptor is selected from the group consisting of NADH, NADPH, thio-NADH, thio-NADPH, acetyl-NADH, and acetyl-NADPH.

8. The method of claim 1, wherein the (2S)-pristanoyl-CoA converting enzyme and the trans-2,3-dehydropristanoyl-CoA converting enzyme are the same.

9. The method of claim 8, wherein both the (2S)-pristanoyl-CoA converting enzyme and the trans-2,3-dehydropristanoyl-CoA converting enzyme are a pristanoyl-CoA dehydrogenase or a trans-2-enoyl-CoA reductase.

10. The method of claim 9, wherein the oxidized form of the first electron acceptor is selected from the group consisting of $NAD^+$, $NADP^+$, thio-$NAD^+$, thio-$NADP^+$, acetyl-$NAD^+$, and acetyl-$NADP^+$; and the reduced form of the second electron acceptor is selected from the group consisting of NADH, NADPH, thio-NADH, thio-NADPH, acetyl-NADH, and acetyl-NADPH.

11. The method of claim 1, wherein the concentration change is assessed by photometric method.

12. The method of claim 1, said method further comprises a step of coupling the oxidized or reduced form of the first electron acceptor or the reduced or oxidized form of the second electron acceptor to a color-producing agent after step c), wherein the concentration change of the oxidized or reduced form of the first electron acceptor or the reduced or oxidized form of the second electron acceptor is assessed by a colorimetric method.

13. The method of claim 1, wherein the sample is a biological sample.

14. The method of claim 13, wherein the biological sample is a blood sample.

15. The method of claim 14, wherein the blood sample is selected from the group consisting of whole blood, serum, and plasma.

16. The method of claim 13, wherein the biological sample is selected from the group consisting of prostate, colon, ovary, breast, bladder, lung, renal, lymphocytes.

17. The method of claim 1, said method is used for prognosis and/or diagnosis of cancer in an individual.

18. The method of claim 17, said method further comprises a step of comparing the amount of alpha-methylacyl-CoA racemase in the sample from the individual to a predetermined value, whereby an increase of the amount of alpha-methylacyl-CoA racemase indicates the individual having or at risk of developing cancer.

19. The method of claim 17, wherein the cancer is selected from the group consisting of prostate cancer, colorectal cancer, ovarian cancer, breast cancer, bladder cancer, lung cancer, renal cancer, lymphoma, and melanoma.

* * * * *